United States Patent

Brois

Patent Number: 5,288,811
Date of Patent: Feb. 22, 1994

[54] CYCLIC CARBONYL CONTAINING COMPOUNDS VIA RADICAL GRAFTING

[75] Inventor: Stanley J. Brois, Westfield, N.J.

[73] Assignee: Exxon Research and Engineering Company, Florham Park, N.J.

[21] Appl. No.: 972,270

[22] Filed: Nov. 5, 1992

[51] Int. Cl.$^5$ .............. C08F 8/12; C08F 8/30; C08F 34/02; C07D 251/00; C07D 309/30; C07C 49/105

[52] U.S. Cl. .............. 525/383; 525/375; 525/385; 525/386; 544/221; 546/155; 548/544; 549/285; 549/292; 549/295; 568/376; 568/379; 528/222; 526/204; 526/213; 526/269

[58] Field of Search .......... 525/386, 375, 383, 333.6, 525/329.9, 330.5, 385; 526/204, 213, 269; 528/222; 544/221, 303; 568/376, 379; 548/544; 549/285, 295, 292; 546/155

[56] References Cited

U.S. PATENT DOCUMENTS 4,897,200  1/1990  Smakman .............. 525/386
5,057,564  10/1991 Brois ..................... 526/269

Primary Examiner—Paul R. Michl
Assistant Examiner—Tae H. Yoon
Attorney, Agent, or Firm—Joseph J. Dvorak

[57] ABSTRACT

Accordingly, novel carbonyl containing compositions are prepared by contacting, in the presence of a free radical initiator, a compound selected from the group consisting of saturated hydrocarbons, substituted saturated hydrocarbons, polymers and mixtures thereof with a carbonyl containing compound or mixtures thereof having the structures:

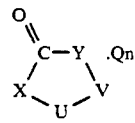

[B]

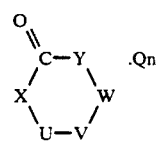

[A]

wherein Q=HOH, MeOH, EtOH, or n-BuOH; n=0,1,>; and X and Y are independently selected from the group consisting of $CH_2$, C=O; W is independently selected from the group consisting of $CH_2$, C=O, O, NH, $CMe_2$, C=N-alkyl and N-alkyl, wherein alkyl is 1 to 18 carbons; U and V are independently selected from the same groups as W and dependently selected so that U and V taken together are one of 1,2-phenylene, 1,8-naphthalene-diyl, and 1,2-naphthalene-diyl.

11 Claims, No Drawings

CYCLIC CARBONYL CONTAINING COMPOUNDS VIA RADICAL GRAFTING

FIELD OF THE INVENTION

The present invention relates to novel carbonyl containing compounds of saturated hydrocarbons, especially polymeric hydrocarbons.

BACKGROUND OF THE INVENTION

In U.S. Pat. No. 5,057,564, novel cyclic carbonyl containing compounds are disclosed. These compounds are produced by heating a mixture of a carbonyl compound having an ene reactive carbonyl group with an unsaturated polymer. Although the process and products are quite useful, it nonetheless would be desirable to be able to form carbonyl modified compounds of saturated hydrocarbons, especially saturated polymers.

SUMMARY OF THE INVENTION

Accordingly, novel carbonyl containing compositions are prepared by contacting, in the presence of a free radical initiator, a compound selected from the group consisting of saturated hydrocarbons, substituted saturated hydrocarbons, polymers and mixtures thereof with a carbonyl containing compound or mixtures thereof having the structures:

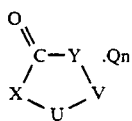

[B]

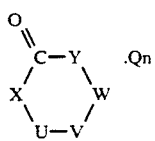

[A]

wherein Q=HOH, MeOH, EtOH, or n-BuOH; n=0,1,>1; and X and Y are independently selected from the group consisting of $CH_2$, C=O; W is independently selected from the group consisting of $CH_2$, C=O, O, NH, $CMe_2$, C=N-alkyl and N-alkyl, wherein alkyl is 1 to 18 carbons; U and V are independently selected from the same groups as W and dependently selected so that U and V taken together are one of 1,2-phenylene, 1,8-naphthalene-diyl, and 1,2-naphthalene-diyl.

In general, the contacting is conducted at a temperature and for a time sufficient to produce the novel compositions.

The compositions prepared according to the method of the invention are particularly useful as solution viscosification agents.

GENERAL DESCRIPTION

According to the present invention, novel carbonyl containing compounds are formed by contacting, in the presence of a free radical initiator, a saturated hydrocarbon or mixtures thereof with a carbonyl containing compound or mixtures thereof having the structures:

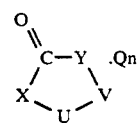

[B]

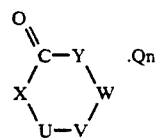

[A]

wherein Q=HOH, MeOH, EtOH, or n-BuOH; n=0,1,>1; and X and Y are independently selected from the group consisting of $CH_2$, C=O; W is independently selected from the group consisting of $CH_2$, C=O, O, NH, $CMe_2$, C=N-alkyl and N-alkyl, wherein alkyl is 1 to 18 carbons; U and V are independently selected from the same groups as W and dependently selected so that U and V taken together are one of 1,2-phenylene, 1,8-naphthalene-diyl, and 1,2-naphthalene-diyl.

Typical carbonyl monomers include alloxan, 1,3-dimethyl-alloxan, indantrione, tetralintetrone, 1,8-naphthalene-trione, cyclopentane-1,2,3-trione, cyclohexane-1,2,3-trione, tetrahydrofuran-2,3,4-trione, pyrrolidine-2,3,4-trione, benzopyran-2,3,4-trione, quinoline-2,3,4-trione, rhodizonic acid, croconic acid, triquinoyl, leuconic acid, isopropylidene ketomalonate, and dehydroascorbic acid derivatives.

Useful free radical initiators used in forming the compounds of this invention include dialkyl peroxides such as di-tertiary-butyl peroxide, 2,5-dimethyl-2,5-di-tertiary-butyl-peroxyhexane, di-cumyl peroxide; alkyl peroxides such as tertiary-butyl hydroperoxide, tertiary-octyl hydroperoxide, cumene hydroperoxide; aroyl peroxides such as such as benzoyl peroxide; peroxyl esters such as tertiary-butyl peroxypivalate, tertiary-butyl perbenzoate; and azo compounds such as azo-bis-isobutyronitrile. Any free radical initiator with a suitable half life at the reaction temperatures cited above can be used.

The radical-initiated reaction of carbonyl monomers can be applied to a wide spectrum of hydrocarbons which can be selected from the group consisting of normal alkanes such as decane, hexadecane, octadecane, tricosane, paraffins having 10 to about 50 carbons; branched alkanes such as dimethyl hexane, trimethyldecane, tetramethylpentadecane [pristane]; white oils, Nujols, hydrogenated oligomers and co-oligomers of ethylene, propylene, butylene and higher molecular weight olefin oligomers having 10 to about 500 carbons; substituted hydrocarbons consisting of normal and branched alkanes having one or more functional groups such as OH, $O[CH_2CH_2O]_xH$, [x=1–10], Cl, CN, COOH, COOalkyl, C[=O]alkyl [alkyl contains 1–18 carbons], aryl, and ethylene groups. Typical examples of useful substituted hydrocarbons consist of decanol, octadecanol, ethoxylated octadecanol, stearic acid, ethyl stearate, methyl decyl ketone, tetrapropylbenzene, octadecene, tetrapropylene, tetraisobutylene, mineral oils, and synthetic lubricant oils.

Useful polymers include but are not limited to polymers derived from one or more of the following monomers: ethylene, propylene, butenes, higher alpha-olefins, styrene, allyl esters, vinyl esters, and halides such as vinyl acetate and vinyl chloride; acrylic acid, acrylonitrile, and the like. Polymers can be linear or branched, and high or low molecular weight ($Mn=500-10$ million). Homopolymers of ethylene such as high and low density polyethylene, atactic or crystalline polypropylene, polybutene, polyisobutylene, homopolymers and copolymers of higher alpha-olefins, copolymers of ethylene with propylene, EPR, which may also contain unconjugated dienes (EPDM), copolymers of ethylene with butenes or higher alphaolefins, copolymers of propylene with butenes, and higher alphaolefins. When dienes such as butadiene, and isoprene are used in copolymer formation, the resulting polymers are preferably hydrogenated to saturate substantially all of the ethylenic unsaturation. Useful polymers include hydrogenated styrene butadiene block, and hydrogenated styrene isoprene block, and star polymers.

Since polymers containing excess ethylenic unsaturation are prone to crosslinking reactions during radical grafting, polymers containing only residual levels of ethylenic unsaturation are preferred.

Typical reaction schemes are illustrated by the following equations:

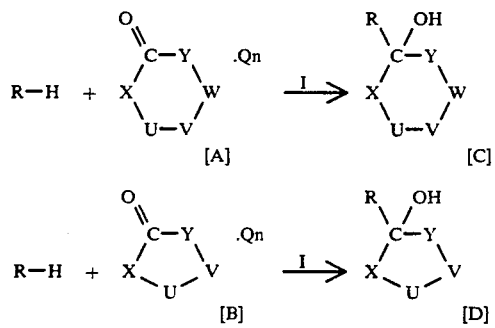

in which R—H represents the hydrocarbon or polymer, I represents the free radical initiator, the structures [A] and [B] represent the cyclic carbonyl compounds, and [C] and [D] represent the radical adducts.

The reaction of the cyclic carbonyl monomer with hydrocarbon and/or polymer substrates can occur in solution, in a melt, and in polymer processing equipment such as a rubber mill, a Bradbender, an extruder, or a Banbury mixer.

Typically, when grafting in solution, the polymer is dissolved in a suitable solvent, such as chlorobenzene, dichlorobenzene, or mineral oil, and heated to temperatures ranging from about 90° C. to about 180° C. depending upon the radical initiator to be used. The carbonyl monomer is added and heated for a suitable period to free any radical-reactive carbonyl groups which may be tied up as a hydrate, alcoholate, or polar solvate. At this point, the radical initiator is added in one dose, or dropwise over a suitable time span, usually from about 5 to 60 minutes. Another option is to add a mixture of the monomer and peroxide in a suitable solvent to the hydrocarbon or polymer solution at an addition rate and suitable reaction temperature consistent with the half life of the radical initiator. The reaction mixture is heated, with stirring, until visual color changes, infrared analysis, and/or nmr analysis indicates that the radical addition of the carbonyl monomer to the hydrocarbon is complete. Grafting reactions with carbonyl monomers such as anhydrous indantrione exhibit characteristic color changes going from lavender, green, yellow, and finally a gold color, which signals complete monomer consumption in the homolytic grafting reaction.

The visible color changes which occur during the addition of hydrocarbyl free radicals to carbonyl monomers such as indantrione, provides a convenient method for monitoring the progress of the grafting reaction. Depending on the temperature and concentration, reaction times of about 0.1 to 12 hours are usually sufficient to achieve high conversions to the radical adducts.

In general, the amount of carbonyl monomer employed is dictated by the level of functionality desired in radical adducts. Levels of radical grafting onto hydrocarbons and polymers ranging from 0.1 wt % to about 20 wt % carbonyl monomer can readily be achieved. Moreover, the high grafting efficiency realized with the carbonyl monomers of the present invention do not usually require the use of excess carbonyl monomer. In addition, the high efficiency of radical grafting of cyclic carbonyl monomers onto hydrocarbons and polymer substrates do not usually require stripping or filtering procedures.

When necessary, functionalized products can be isolated by solvent removal using evaporative techniques, or in the case of functional polymers, by adding the reaction mixture to a polar solvent such as acetone or methanol, which induce the precipitation of the functionalized polymer.

Radical grafting of polymers may also be conducted without a solvent, as in a melt, or in polymer processing equipment such as a rubber mill, an extruder, a Banbury mixer, Brabender mixer, and the like. When radical grafting is conducted in bulk, reaction temperatures ranging from about 90° C. to about 220° C., and reaction times ranging from about .05 to about 1 hour are typical.

The amount of free radical initiator used is generally between 1 and 100 wt % based on the weight of the carbonyl monomer, and often depends upon the nature of the free radical initiator, and hydrocarbon or polymer substrate being grafted. The susceptibility of certain polymers to undergo crosslinking and/or chain scission necessitates requires careful discretion regarding reagent concentrations, time, temperature, and process conditions since these parameters are all dependent variables in the grafting process. Ordinarily, grafting processes which use from about 10 wt % to about 50 wt % levels of free radical initiator, at grafting temperatures ranging from about 120° C. to about 180° C., in an oxygen-free reactor can produce functional polymers with significant levels of appended carbonyl monomers.

EXAMPLES

Example 1

A mixture of 34.1 grams of n-decane and 1 gram of indantrione (IT) was heated to 160° C. under a nitrogen atmosphere. Some of the IT which dissolved imparted a green color to the reaction mixture at 160° C. After adding 0.5 ml of t-butyl peroxide (in a single dose from a graduated pipette), to the stirred mixture at 160° C., the IT gradually dissolved and, over a period of about 10 minutes, a golden-colored solution was obtained. After heating for an hour at 160° C., the solution was rotoevaporated. The residue featured an infrared spectrum with a strong carbonyl absorption band at 5.8 microns, a UV-visible spectrum with a strong absorption band at 226.5 nm, and a gc-mass spectrum displaying several isomers having a molecular ion at $m/e=302$.

Example 2

A 100 ml three-necked round bottom flask equipped with magnetic stirrer, thermometer, reflux condensor, and dropping funnel, was charged with 34.1 ml of pristane (2,6,10,14-tetramethylpentadecane), and 1.0 gram of anhydrous ninhydrin. Gradually heating the stirred mixture to 150° C. dissolved the purple ninhydrin, and gave a dark blue solution. When the reaction temperature reached 160° C., 0.5 ml of di-tert-butyl peroxide was added in one portion, via a graduated pipette, to the stirred reaction solution. The reaction temperature spontaneously climbed to 163° C., and the color of the solution turned from dark blue to green, to yellow and ultimately orange in about 8 minutes.

Vacuum distillation of the mixture afforded a residue which featured an infrared spectrum with a prominent carbonyl absorption band at 5.85 microns, a gc-mass spectrum showing isomers with a molecular ion at m/e=428, and a carbon magnetic resonance spectrum consistent with a mixture of isomers derived from the radical addition of pristane to indan-1,2,3-trione.

Example 3

A mixture of 1 gram of indantrione, 10 ml of pristane, and 20 grams of 1,2-dichlorobenzene was combined in a stirred reactor under nitrogen, and heated to 160° C. until a clear, dark green solution was obtained. The free radical initiator (1 ml of t-butyl peroxide) was added dropwise over a span of 5 minutes. During this period, the color of the solution changed from green, to yellow, and finally a bright orange. Heating was continued at 160° C. for a half hour, and the solution was rotoevaporated. Gc-mass spectral analysis of the residue showed the presence of isomers arising from the addition of pristane radicals to indantrione. The UV-visible spectrum of the product featured a strong absorption band at 295 nm.

Example 4

A mixture of one gram of indantrione, 20 ml of 1,2-dichlorobenzene, and 10 ml of n-nonanol was added to a 50 ml, three-necked round bottom flask equipped with magnetic stirrer, condenser, and addition funnel. The mixture was stirred at 160° C. until a clear dark, green solution was obtained. With the aid of a micro-pipette, one ml of t-butyl peroxide was added in one dose to the stirred dark green solution at 160° C. Over a span of 11 minutes, the color of the solution changed from dark green, to gold, and finally a bright orange. Rotoevaporation afforded a residue which featured an infrared spectrum with a hydroxyl absorption band at about 3 microns, and a carbonyl absorption band at 5.8 microns, and a mass spectrum which confirms the presence of isomeric adducts arising from the free radical addition of n-nonanol to indantrione.

Example 5

Following the method of Example 7, ethyl caproate was reacted with indantrione to afford a product with infrared and mass spectra consistent with the radical addition of the ester to indantrione.

Example 6

A mixture of 1 gram of 1,3-dimethylalloxan, 20 grams of 1,2-dichlorobenzene, and 10 ml of pristane were combined in a nitro gen-blanketed 100 ml round bottom flask equipped with a condenser, magnetic stirrer, thermometer, and dropping funnel. When the temperature reached 160° C., the radical initiator, t-butyl peroxide (0.5 ml) was added all at once, and the mixture was stirred at 160° C. until a clear solution was obtained (about an hour). Rotoevaporation of the solution gave a residue which featured an infrared spectrum with an intense carbonyl absorption band at 5.9 microns, and a mass spectrum which confirmed the presence of an adduct formed via the radical addition of pristane to dimethylalloxan.

Example 7

Following the general method of Example 9, alloxan was induced to add separately to radicals generated from octadecane and pristane, to give isomeric mixtures of 5-octadecyl- and 5-pristyl-5-hydroxy-barbituric acid, respectively. Each of the radical adducts displayed an infrared spectrum with a strong carbonyl absorption band at 5.9 mirons, and a mass spectrum consistent with the proposed radical adducts.

Example 8

A mixture of 10 grams of polyisobutylene (Mn=950), 20 ml of 1,2-dichloro-benzene, and 2 grams of indantrione hydrate were combined in a reactor blanketed with a nitrogen atmosphere, mechanically stirred, and heated to 160° C. The initiator, t-butyl peroxide (0.5 ml) was added dropwise over a span of 15 minutes, to the dark-green colored mixture being stirred at 160° C. During this period, the color of the mixture changed from green to gold. Heating was continued for about 2 more hours. The cooled mixture was diluted with 200 ml of cyclohexane, filtered twice, and concentrated by rotoevaporation. The residue featured an infrared spectrum with a strong carbonyl absorption band at 5.8 microns, and analyzed for 3.50% oxygen.

Example 9

In a manner similar to Example 11, except that no solvent was used, 13 grams of polyisobutylene (Mn=1300) were radically grafted with 1.6 grams of anhydrous indantrione at 160° C. via initiation with a half ml of t-butyl peroxide. Heating for several hours gave a dark-brown reaction mixture which was cooled, diluted with 200 ml of cyclohexane, and filtered. Rotoevaporation of the filtrate afforded a residue which featured a prominent carbonyl absorption band at 5.8 microns, and analyzed for 3.05% oxygen.

Example 10

A mixture of 22.5 grams of polyisobutylene (Mn=2250) and 1.6 grams of purple-colored indantrione was heated to 160° C., and then treated with 0.10 ml of initiator (t-butyl peroxide) in one dose. After stirring at 160° C. for three hours, the reaction mixture was cooled, diluted with 200 ml of cyclohexane, and filtered twice. Rotoevaporation of the filtrate afforded a residue which featured a strong carbonyl absorption band at 5.8 microns, and analyzed for 2.2% oxygen.

Example 11

A 10 gram sample of polyisobutylene (Mn=950) was charged into a reactor blanketed with nitrogen, and heated to 170° C. Twenty mls of a dioxane solution containing 1.6 grams of anhydrous alloxan and 1.0 ml of t-butyl peroxide were added dropwise to the stirred polyisobutylene at 170° C. over a period of an hour. The temperature was maintained at 170° C. by allowing the dioxane to distill out of the reactor as the dioxane solution was added. After heating at 170° C. for 4 hours, the reaction mixture was cooled, diluted with about 200 ml of cyclohexane, and filtered. Rotoevaporation afforded a residue which featured an infrared spectrum with a strong carbonyl absorption band at 5.9 microns, and analyzed for 1.62% nitrogen.

Example 12

Sublimed 1,3-dimethyl-alloxan (1.7 grams) monomer was grafted onto polyisobutylene (Mn=950) by combining the monomer with 10 grams of the polyisobutylene and 20 ml of 1,2-dichlorobenzene, heating the mixture to 160° C., and initiating the radical process by adding dropwise, 0.5 ml of t-butyl peroxide. The resulting solution was heated for 4 hours, cooled, diluted with 300 ml of cyclohexane and filtered. Rotoevaporation of the filtrate gave a residue which featured an infrared spectrum with a carbonyl band at 5.9 microns, and analyzed for 1.48% nitrogen.

Example 13

Ten grams of an ethylene-propylene copolymer containing 55 wt % propylene, and having an Mn=54,000 were modified with 1 gram of anhydrous indantrione, by dissolving both reagents in 90 ml of 1,2-dichlorobenzene at about 160° C. The addition of 0.5 ml of t-butyl peroxide causes the green solution to change to an orange gold color, and become very viscous over the course of 15 minutes. The addition of 50 ml of dichlorobenzene thinned out the solution (no gel formation was observed) and stirring at 160° C. was continued for 4 hours. The cooled solution was diluted with 100 ml of cyclohexane, and added slowly to a liter of acetone. The precipitated polymer was redissolved in cyclohexane and again precipitated from a large volume of acetone, and dried in a vacuum oven at 40° C. overnight. The polymer featured an infrared spectrum (film) with a prominent carbonyl absorption at 5.8 microns, and analyzed for 2.10% oxygen.

Example 14

A 10 gram sample of the ethylene-propylene copolymer used in Example 16 and 90 grams of dichlorobenzene were charged into a reactor blanketed with nitrogen and heated to 150° C. Twenty mls of a dioxane solution containing 1 gram of anhydrous alloxan and 0.5 ml of t-butyl peroxide were added dropwise to the stirred polymer solution at 160° C. over a 15 minute period. The temperature was maintained at 160° C. by allowing the dioxane to distill out of the reactor as the dioxane solution was added. After heating at 160° C. for about 2 hours, the reaction mixture was cooled, diluted with about 200 ml of cyclohexane and slowly added to a liter of acetone to precipitate the functionalized polymer. The orange-colored polymer was redissolved in cyclohexane and again added to a large volume of acetone. The precipitated polymer was dried in a vacuum oven at 40° C. overnight. The dried polymer featured an infrared spectrum with a strong carbonyl absorption band at 5.9 microns, and analyzed for 0.65% nitrogen.

Example 15

Ten grams of a hydrogenated poly-alpha-olefin, specifically, polydecene-1 [Mn=ca. 4000], dissolved in 40 grams of dichlorobenzene, and a half gram of anhydrous indantrione dissolved in 50 grams of dichlorobenzene were combined in a nitrogen-blanketed reactor, and heated to about 160° C. One ml of t-butyl peroxide was added in one dose to the stirred, green solution maintained at about 160° C. In about 15 minutes, the color of the solution changed from green to gold indicating that the indantrione monomer was completely consumed in the radical-promoted grafting reaction. Rotoevaporation gave a residue which featured an infrared spectrum dominated by a strong ketone carbonyl absorption at about 5.8 microns, a uv-gel permeation chromatogram confirming the presence of a functional polymer featuring the same polydispersity as the starting polymer, and an elemental analysis indicating that the funcational polymer contained 2.2% oxygen.

Example 16

Ten grams of a polyester basestock (peak MW=427) obtained by esterifying pentaerythritol with a mixture of alkanoic acids, and one gram of anhydrous indantrione were combined in a nitrogen-blanketed reactor, and heated to about 160° C. until the indantrione monomer dissolved. About one ml of t-butyl peroxide was added in one dose to the stirred green solution maintained at about 160° C. After an hour, the color of the solution changed from green to gold. Analysis of the cooled residue by thermal spray MS revealed that the indantrione added to the polyester basestock.

Example 17

Ten grams of a hydrogenated star-shaped polyisoprene polymer dissolved in 90 grams of chlorobenzene, and 0.25 gram of anhydrous indantrione dissolved in 100 grams of chlorobenzene were combined in a nitrogen-blanketed reactor, and heated to about 100° C. Half a gram of t-butyl peroxypivalate was added in one dose to the stirred green solution, and after 70 minutes, the color of the solution changed from green to gold. The isolated polymer featured an infrared spectrum with a carbonyl absorption band at 5.8 microns, and analyzed for 2.18 oxygen.

Example 18

Ten grams of a star-shaped polyisoprene polymer and 0.25 gram of anhydrous indantrione were dissolved in 190 grams of dichlorobenzene at 160° C. in a nitrogen-blanketed reactor. The green solution was treated with 0.25 ml of t-butyl peroxide in one dose, and within 40 minutes, changed in color from green to gold. The isolated polymer featured an infrared spectrum with a strong carbonyl absorption band at 5.8 microns, and analyzed for 1.09% oxygen.

What is claimed is:

1. A carbonyl containing composition formed by contacting, in the presence of a free radical initiator, a compound selected from the group consisting of saturated hydrocarbons, substituted saturated hydrocarbons, polymers and mixtures thereof with a carbonyl containing compound or mixtures thereof having the structures:

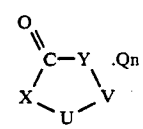

and

-continued

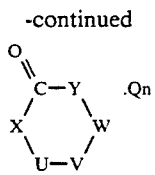

wherein Q=HOH, MeOH, EtOH, or n-BuOH, n=0,1,>1; and X and Y are independently selected from the group consisting of CH₂, C=O; W is independently selected from the group consisting of CH₂, C=O, O, NH, CMe₂, C=N-alkyl and N-alkyl, wherein alkyl is 1 to 18 carbons; U and V are independently selected from the same groups as W and dependently selected so that U and V taken together are one of 1,2-phenylene, 1,8-napthalene-diyl, and 1,2-napthalene-diyl, provided that at least one of X, Y, U, V and W is C=O.

2. The composition of claim 1 wherein said contacting is at a temperature of from about 90° to about 220° C.

3. The composition of claim 2 wherein said hydrocarbon has about 10 to about 50 carbon atoms.

4. The composition of claim 2 wherein said hydrocarbon is a polymer having a Mn of from about 500 to about 10 million.

5. The composition of claim 3 or 4 wherein said carbonyl compound has the formula:

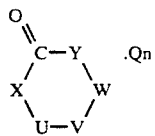  [A]

6. The composition of claim 3 or 4 wherein said carbonyl compound has the formula:

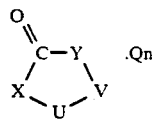  [B]

7. A composition of matter comprising:
(a) a hydrocarbon radical, and
(b) a cyclic radical selected from the group consisting of

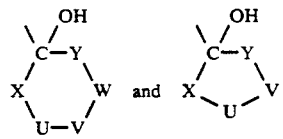

wherein Q=HOH, MeOH, EtOH, or n-BuOH; n=0,1>1; and X and Y are independently selected from the group consisting of CH₂, C=O; W is independently selected from the group consisting of CH₂, C=O, O, NH, CMe₂, C=N-alkyl and N-alkyl, wherein alkyl is 1 to 18 carbons; U and V are independently selected from the same groups as W and dependently so that U and V taken together are one of 1,2-phenylene, 1,8- naphthalene-diyl, and 1,2-naphthalene-diyl, provided that at least one of X, Y, U, V and W is C=O.

8. The composition of claim 7 wherein the hydrocarbon radical is selected from he group consisting of saturated hydrocarbons, substituted saturated hydrocarbons, and polymers.

9. The composition of claim 8 wherein the saturated hydrocarbons have from about 10 to about 500 carbon atoms.

10. The composition of claim 8 wherein the substituted hydrocarbons have at least one functional group selected from the group consisting of OH, O[OH₂C-H₂O]xH where x is from 1 to 10, Cl, CN, COOH, COOalkyl where the alkyl has 1 to 18 carbons, aryl and ethylene.

11. The composition of claim 8 wherein the polymers have number average molecular weight in the range of from about 500 to 10 million and are selected from the group consisting of polyolefin, polyalkyl esters, polystyrene, polyacrylates and polyvinyl halides and eaters.

* * * * *